US00RE48822E

(19) United States
(12) Reissued Patent
Siminou et al.

(10) Patent Number: US RE48,822 E
(45) Date of Reissued Patent: *Nov. 23, 2021

(54) INTELLIGENT PATIENT INTERFACE FOR OPHTHALMIC INSTRUMENTS

(75) Inventors: Kamran Siminou, Newport Coast, CA (US); Jeffrey Oliver, Cedar Park, TX (US)

(73) Assignee: NEUROPTICS, INC., Irvine, CA (US)

( * ) Notice: This patent is subject to a terminal disclaimer.

(21) Appl. No.: 13/543,832

(22) Filed: Jul. 8, 2012

Related U.S. Patent Documents

Reissue of:
(64) Patent No.: 7,753,527
Issued: Jul. 13, 2010
Appl. No.: 12/367,513
Filed: Feb. 7, 2009

U.S. Applications:
(63) Continuation of application No. 11/800,333, filed on May 5, 2007, now Pat. No. 7,488,074, which is a continuation of application No. 10/643,280, filed on Aug. 18, 2003, now Pat. No. 7,216,985.

(60) Provisional application No. 60/405,287, filed on Aug. 21, 2002.

(51) Int. Cl.
*A61B 3/18* (2006.01)
*A61B 3/00* (2006.01)

(52) U.S. Cl.
CPC ..... *A61B 3/18* (2013.01); *A61B 3/0083* (2013.01)

(58) Field of Classification Search
CPC ..... A61B 3/0083
USPC ..... 359/600; 351/200, 205, 206, 245
See application file for complete search history.

(56) References Cited

U.S. PATENT DOCUMENTS 5,903,336 A * 5/1999 Kohayakawa ..... 351/245
6,022,109 A * 2/2000 Dal Santo ..... A61B 3/112 351/221
6,025,725 A * 2/2000 Gershenfeld ..... H01F 17/0006 324/652
6,580,555 B2 * 6/2003 Crista ..... 359/426
6,650,305 B1 * 11/2003 Havey ..... G06F 1/1601 345/158
7,329,003 B2 * 2/2008 Nicolini ..... A61B 3/028 108/43
2001/0041884 A1 * 11/2001 Frey et al. ..... 606/5
2002/0024675 A1 * 2/2002 Foxlin ..... 356/620
2003/0224729 A1 * 12/2003 Arnold ..... G08C 17/02 455/59
2004/0032490 A1 * 2/2004 Uchida ..... H04N 5/361 348/96
2005/0212948 A1 * 9/2005 Watanabe ..... H04N 5/23245 348/340
2009/0128934 A1 * 5/2009 Plangger ..... G02B 21/362 359/827
2009/0192389 A1 * 7/2009 Eilers ..... A61B 3/1005 600/459

(Continued)

FOREIGN PATENT DOCUMENTS

WO WO 99/53621 * 10/1999 ..... H04B 1/38

*Primary Examiner* — Fred O Ferris, III
(74) *Attorney, Agent, or Firm* — Hybrid Law Group P.C.

(57) ABSTRACT

An ophthalmic examination system comprising a headrest with a detection element, and an ophthalmic instrument (OI) having a microprocessor and a sensor in communication with the microprocessor. The sensor is configured to detect the presence of the detection element, and the headrest is configured for coupling to the OI.

1 Claim, 5 Drawing Sheets

(56) References Cited

U.S. PATENT DOCUMENTS

| | | | | |
|---|---|---|---|---|
| 2009/0195363 | A1* | 8/2009 | Downie | G06K 5/02 340/10.4 |
| 2009/0247993 | A1* | 10/2009 | Kirschenman | A61M 25/0147 606/1 |

* cited by examiner

INTELLIGENT PATIENT INTERFACE FOR OPHTHALMIC INSTRUMENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO PRIORITY DOCUMENT

*This is a reissue of U.S. Pat. No. 7,753,527, which issued from U.S. application Ser. No. 12/367,513, filed Feb. 7, 2009.*

This is a continuation of U.S. application Ser. No. 11/800,333, filed on May 5, 2007, which is a continuation of U.S. Pat. No. 7,216,985, filed on Aug. 18, 2003, which claims priority from U.S. Provisional Patent Application No. 60/405,287, entitled "Intelligent Patient Interface for Ophthalmic Instruments", filed on Aug. 21, 2002. Priority of the aforementioned filing dates is hereby claimed, and the disclosures of the earlier applications are hereby incorporated by reference in their entirety.

BACKGROUND OF THE INVENTION

1. Field of the Invention

The present invention relates generally to ophthalmic instruments such as pupilometers, and, more particularly, to intelligent headrests configured to couple with pupilometers and ocular examination equipment.

2. Description of the Related Art

Most ophthalmic instruments, including pupilometers, have patient interfaces such as eyecups. However, eyecups presently are dumb devices. That is, their only function is to enable an ophthalmic instrument to be positioned in close proximity to an individual's eye and to isolate the eye. They are usually attached by simple attaching means or are integrated into ophthalmic instruments, but have no means of communicating with the instruments to which they are attached.

Devices, such as pupilometers, are used to monitor and detect various optical characteristics. For example, U.S. Pat. Nos. 6,260,968 and 6,116,736 (the entireties of both which are incorporated herein by reference), as well as U.S. application Ser. No. 09/711,675, filed Nov. 9, 2000 (the entirety of which is incorporated herein by reference), all disclose pupilometers that are used to detect papillary irregularity. They are often used with eyecups so that the examiner can isolate the pupil. However, the state of the art in eyecups does not permit communication between the eyecup and the pupilometer such that the pupilometer obtains information about the patient from the eyecup being used.

Intelligent headrests and eyecups can be useful for providing information about certain characteristics of the individual being examined, such as whether or not the individual is an adult or a child. Such information can be very useful for calibrating the ophthalmic instrument.

There is a need for headrests that can communicate with the ophthalmic instruments, such as pupilometers, and can provide information about the individual being examined. Such headrests may provide medical practitioners with improved ocular data. Likewise, there is a need for intelligent headrest/ophthalmic instrument systems that are capable of providing medical practitioners with improved ocular data.

SUMMARY

In accordance with one aspect of the invention, a headrest for use with an ophthalmic instrument is described. In one embodiment, the headrest includes a distal plate and at least one arm projecting proximally from the distal plate. A face pad is attached to the end of the with arm for resting the headrest against an individual's face. The distal plate has a central aperture and an attachment slot for attaching the headrest to an ophthalmic instrument. At least one detection element is integrated with the distal plate. The detection element can be a magnet, a LED, an optical filter, a metal projection, a radio frequency transmitter, or any other mechanism that can be detected by a sensor on an ophthalmic instrument.

In another embodiment, the headrest includes an ophthalmic instrument connector, a rotation ring connected to the ophthalmic instrument connector, and an eyecup connected to the rotation ring. The rotation ring includes at least one receptacle that receives a detection element.

In accordance with another aspect of the invention, an ophthalmic examination system comprises a headrest having a detection element and an ophthalmic instrument (OI) comprising a microprocessor and a sensor in communication with the microprocessor. The sensor can be configured to detect the presence of the detection element, and the headrest can be configured for coupling to the OI. The OI can be a pupilometer, glaucometer, opthalmoscope, or any other ophthalmic instrument now known or later invented. The OI and the headrest can communicate via the detection element and the sensor.

In one embodiment, the detection element is made up of one, two, three, four, five, six, seven, eight, nine, ten, or more magnets, and the sensor is made up of one, two three, four, five, six, seven, eight, nine, ten, or more Hall-effect sensors.

In another embodiment, the detection element is made up of one, two, three, four, five, six, seven, eight, nine, ten, or more LEDS, and the sensor is made up of one, two, three, four, five, six, seven, eight, nine, ten, or more photo detectors.

In another embodiment, the detection element is made up of one, two, three, four, five, six, seven, eight, nine, ten, or more optical filters, and the sensor is made up of one, two, three, four, five, six, seven, eight, nine, ten, or more special photo-detectors.

In another embodiment, the detection element is made up of one, two, three, four, five, six, seven, eight, nine, ten, or more metal projections, and the sensor is made up of one, two, three, four, five, six, seven, eight, nine, ten, or more switches that can be shorted by the one or more metal projections.

In another embodiment, the detection element is made up of a radio-frequency transmitter, and the sensor is made up of a radio frequency receiver.

In another embodiment, the detection element is made up of a microprocessor having a memory, and the sensor is made up of an interface between the OI and the headrest. When the headrest is coupled to the OI, it can interface with the OI through an interface, such as any of those known in the computer arts, including but not limited to a parallel port, a serial port, a universal serial bus, an optical interface, an RF interface or an extension of photodiodes and detectors (linear array), reading a bar-code which is part of the headrest, or a programmed magnetic strip or radio transmission contained in the headrest, or any other type of interface known in the art. Thus, information between the microprocessor in the headrest and the microprocessor in the OI can be shared. The information can include a unique code to identify the type of headrest being used. For example, a headrest for a child or infant can have a unique identifier that can distinguish it from a headrest made for an adult. In addition, the headrest can be programmed using programming means provided in the OI when the headrest and OI are attached.

In another aspect of the invention, an OI has a detachable headrest, a microprocessor, and a sensor in communication with the microprocessor. The detachable headrest can include a detection element, and the sensor can be configured to detect the presence of the detection element. The OI can be a pupilometer, glaucometer, opthalmoscope, or any other ophthalmic instrument now known or later invented. The headrest can communicate with the rest of the OI via the detection element and the sensor.

In one embodiment, the detection element is made up of one, two, three, four, five, six, seven, eight, nine, ten, or more magnets, and the sensor is made up of one, two, three, four, five, six, seven, eight, nine, ten, or more Hall-effect sensors.

In another embodiment, the detection element is made up of one, two, three, four, five, six, seven, eight, nine, ten, or more LEDS, and the sensor is made up of one, two, three, four, five, six, seven, eight, nine, ten, or more photo detectors.

In another embodiment, the detection element is made up of one, two, three, four, five, six, seven, eight, nine, ten, or more special photo-detectors.

In another embodiment, the detection element is made up of one, two, three, four, five, six, seven, eight, nine, ten, or more metal projections.

In another embodiment, the detection element is made up of a radio-frequency transmitter, and the sensor is made up of a radio frequency receiver.

Other objects and features of the present invention will become apparent from consideration of the following description taken in conjunction with the accompanying drawings.

BRIEF DESCRIPTION OF DRAWINGS

Reference is next made to a brief description of the drawings, which are intended to illustrate an ophthalmic examination system and ophthalmic examination instruments having intelligent headrests. The drawings and detailed description which follow are intended to be merely illustrative and are not intended to limit the scope of the invention as set forth in the appended claims.

DETAILED DESCRIPTION

In one embodiment, an ophthalmic examination system is intended to enable an OI that measures information from the eye to detect whether a headrest or other ophthalmic patient interface like an eyecup or stimulation source is attached and further to determine the type of headrest that is attached (e.g., pediatric open-air, adult open-air, eyecup with orientation sensitivity, eyecup with finger ports, etc.). Based on the information unique to the patient interface, the OI can self-configure for the type of measurement to be made and calibrate accordingly. In addition to calibration, information regarding ambient light levels at the pupil can be determined. For example, the use of an enclosed opaque eyecup would shield the eye being measured from most ambient light thus allowing dark adapted measurements in a lighted room. In addition, if the headrest is not detected the OI will be prevented from taking measurements in order to avoid inaccurate measurements. In some cases, the risk of cross-contamination may be reduced where unique patient information is actually stored in a memory device which is integrated into the headrest.

For example, if the OI is a Neuroptics pupilometer, such as those shown in U.S. Pat. Nos. 6,116,736 and 6,260,968, as well as U.S. application Ser. No. 09/711,675, filed Nov. 9, 2000, all of which are incorporated herein by reference, it is beneficial for the pupilometer to know whether or not the headrest is attached to it. If it is not attached and measurements can be taken, these measurements may not be as accurate as they would otherwise be if the headrest is attached.

Several different types of headrests are contemplated (e.g., adult vs. pediatric or closed eyecup vs. open eyecup). It can be beneficial to know which headrest is attached to the pupilometer, because the pupilometer can calibrate itself according to the different parameters of adult verses pediatric patients. Likewise, if the pupilometer can detect whether the headrest is an open vs. closed eyecup, information regarding the amount of ambient light which surrounds the eye can be determined and the pupilometer calibrated in accordance therewith. This can be useful in determining the expected versus measured size/reactivity of the eye. Thus, the OI can be configured to implement software algorithms (i.e., reconfigure itself for intended use) based upon information received from the headrest.

One example of self-configuration is the ability to change the choice of the targeted eye according to the orientation of the headrest; so that mechanical rotation from right-to-left is reflected automatically in the software.

Figure 1:
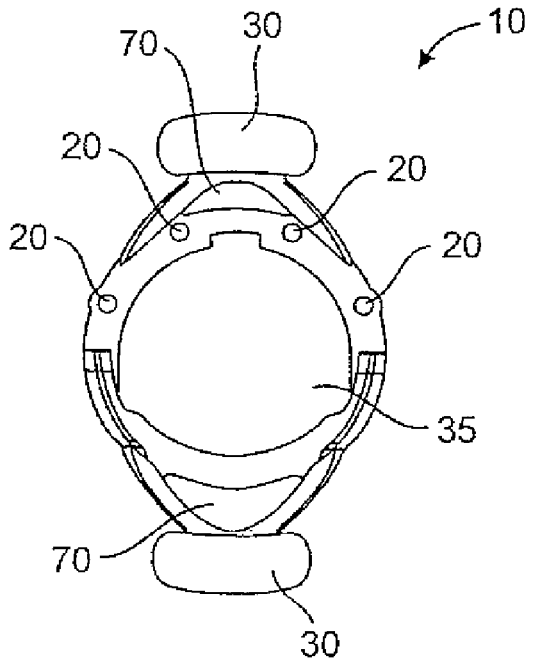
FIG. 1 is a top view of a headrest according to one embodiment.
Figure 2:
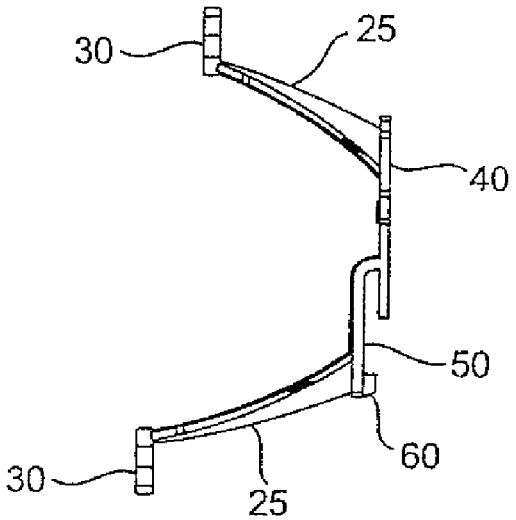
FIG. 2 is a side elevational view of the headrest depicted in FIG. 1.
Figure 3:
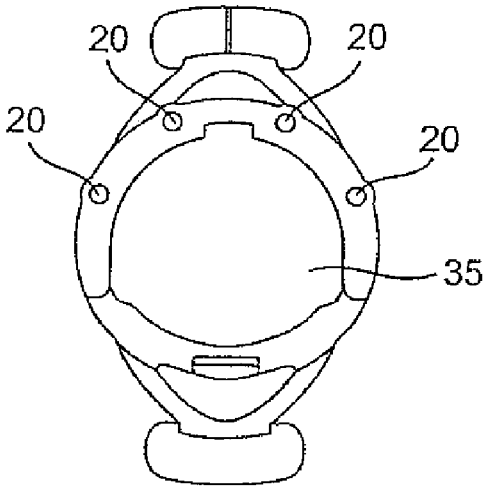
FIG. 3 is a bottom view of the headrest depicted in FIG. 1.

FIGS. 1-3 show a headrest 10 that can be attached to different ophthalmic instruments. The headrest 10 includes an attachment plate 40. The attachment plate 40 has a central aperture 35. The attachment plate connects to the lens or face plate of an ophthalmic instrument, and the central aperture 35 provides the ophthalmic instrument with a window to an individual's eye.

Just below the attachment plate 40 is an attachment slot 50 and connection lip 60, which are configured for connection to an ophthalmic instrument. Other modes of connection can also be used. Arms 25 project from the attachment plate at an angle of about one hundred degrees relative to the attachment plate. Face pads 30 are integrally formed or otherwise connected to the ends of the arms 25. The face pads 30 are adapted for bracing the headrest 10 against an individual's face, particularly around an eye during examination. The headrest 10 also has openings 70 formed into the arms 25, which allow light to pass through to the eye.

Detection elements 20 are integrated into the attachment plate 40. FIGS. 1-3 show four detection elements 20, but more than four or less than four detection elements can also be used. The detection elements, as further described below, can be magnets, LEDS, optical filters, metal projections, radio frequency transmitters, or any other mechanism that can be detected by a sensor built into an ophthalmic instrument.

The headrest 10 can be used in combination with an OI that senses the presence of a given headrest, and determines the type of headrest being used. The OI can include a sensor integrated therewith which can sense a detection element integrated into the headrest. For example, FIGS. 1-3 show a headrest 10, which is configured to be coupled or attached to an OI (not shown), such as a pupilometer, glaucometer, opthalmoscope, or any other ophthalmic examination instrument, such as any of the pupilometers disclosed in U.S. Pat. Nos. 6,116,736 and 6,260,968, as well as U.S. application Ser. No. 09/711,675, filed Nov. 9, 2000, all of which are incorporated herein by reference. As explained above, a connection slot 50 and connection lip 60 are configured for connection to an OI.

In one embodiment, the OI includes a Hall-effect sensor with one, two, three, four, five, six, seven, eight, nine or more Hall-effect switches integrated into its design. The Hall-effect switches can detect the presence of a magnetic field. The detection elements 20 on the headrest 10 can be magnets embedded in the headrest 10, such that when the headrest 10 is attached or coupled to the OI, the magnets 20 line up with the Hall-effect switches, and the Hall-effect sensor will be able to detect the magnets in the headrest. The Hall-effect switches can be in communication with a microprocessor, such that the microprocessor receives information about the number and orientation of the magnets in the headrest. The microprocessor will include programming configured to process that information to determine the presence and type of headrest being used. For example, the use of n magnets and n number Hall-effect switches allows for 2"-1 types of headrests with "n" defined as the number of magnets and Hall-effect switches. Thus, if there are four magnets and four Hall-effect switches, the microprocessor of the OI can identify up to fifteen different varieties of headrests.

In another embodiment, the detection elements 20 can be LEDS or they can alternatively be optical filters. According to such embodiments, the corresponding sensor in the OI could be a photo detector. The system can be configured so that there are up to four LEDS in the headrest 10 and four corresponding photo detectors in the OI that line up with the LEDS, thus leading the OI's microprocessor to identify up to fifteen different types of headrests based on the equation 2"-1, where n" is defined as the number of LEDS or optical filters and photo detectors. Of course there can be more than four LEDS and photo detectors, thus increasing the number of possible headrests based on the equation 2"-1.

Alternatively, there can be one LED emitting any number of different wavelengths of light, each wavelength corresponding to a different type of headrest. The wavelength sensed by the photo detector is transmitted to the microprocessor, which can include programming configured to process that information and to determine the presence and type of headrest being used.

In another embodiment, the headrest 10 includes detection elements 20, which are metal projections. For example, and as shown in FIGS. 1-3, there can be up to four metal projections that are adapted to contact four corresponding switches in the OI. Like in the above examples, the OI's microprocessor can then detect up to fifteen different types of headrests based on the equation 2"-1 where "n" is defined as the number of metal projections and corresponding switches. Of course, there can be more than four metal projections and switches, thus increasing the number of possible headrests based on the equation 2"-1.

In another embodiment, the OI includes one, two, three, four, five, six, seven, eight, nine, or more LEDS integrated into its design. The OI also includes one, two, three, four, five, six, seven, eight, nine or more photo detectors. The corresponding detection elements in the head rest can be mirrors, which reflect light emitted by the LEDS back to the photo detectors. The position and number of mirrors dictates the type of headrest being used. The photo detectors detect the light being reflected by the mirrors and transmit signals to the microprocessor, which can process the information to determine the presence and type of headrest being used.

In yet another embodiment, the detection element in the headrest can be a radio frequency transmitter. The corresponding sensor in the OI can be a radio frequency receiver coupled to the microprocessor of the OI. The receiver can detect the frequency being emitted by the transmitter and send that information to the microprocessor, which can include programming for processing that information to determine the presence and type of headrest being used.

Figure 4:
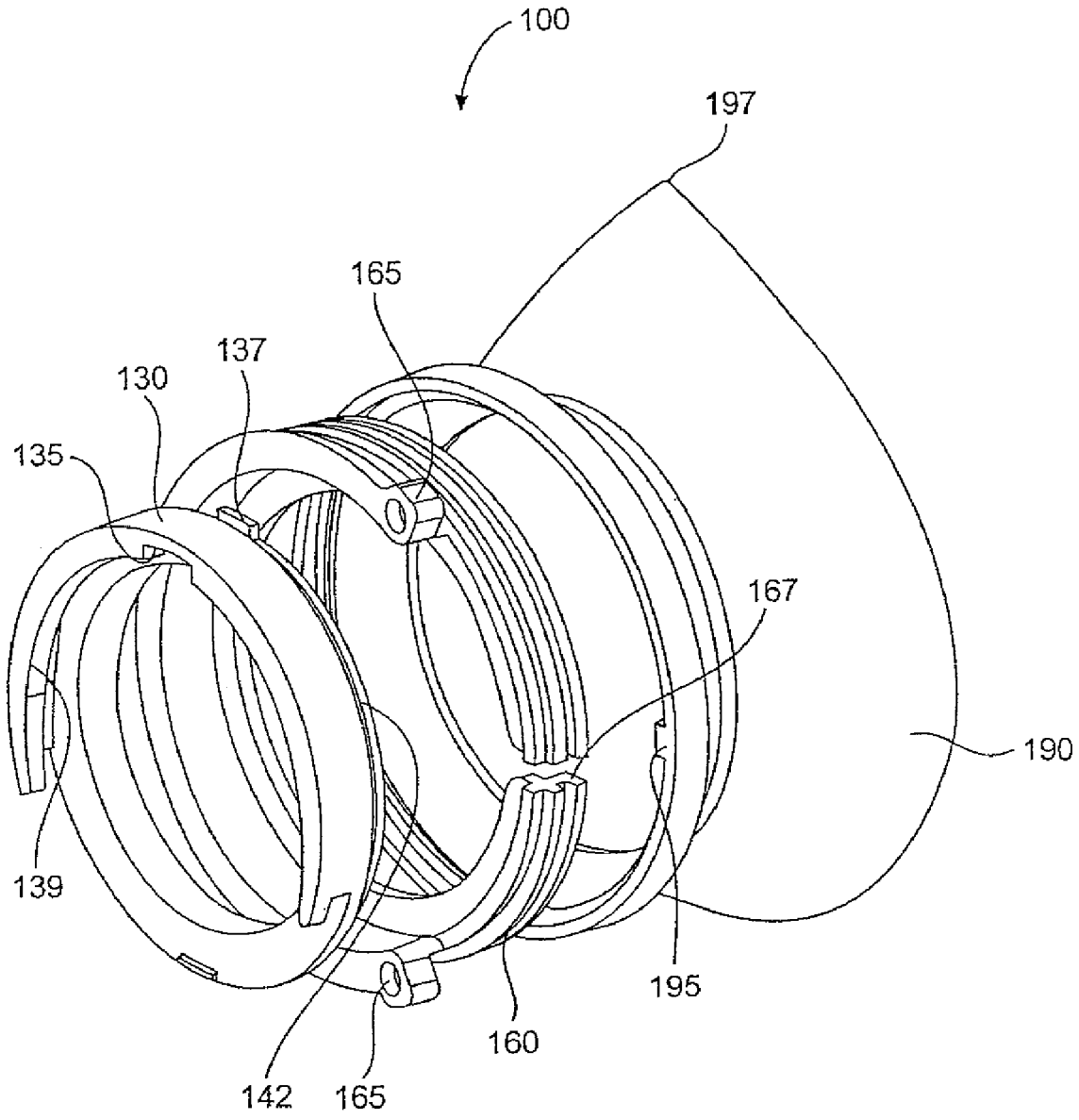
FIG. 4 is an exploded view of a headrest according to another embodiment.
Figure 5:
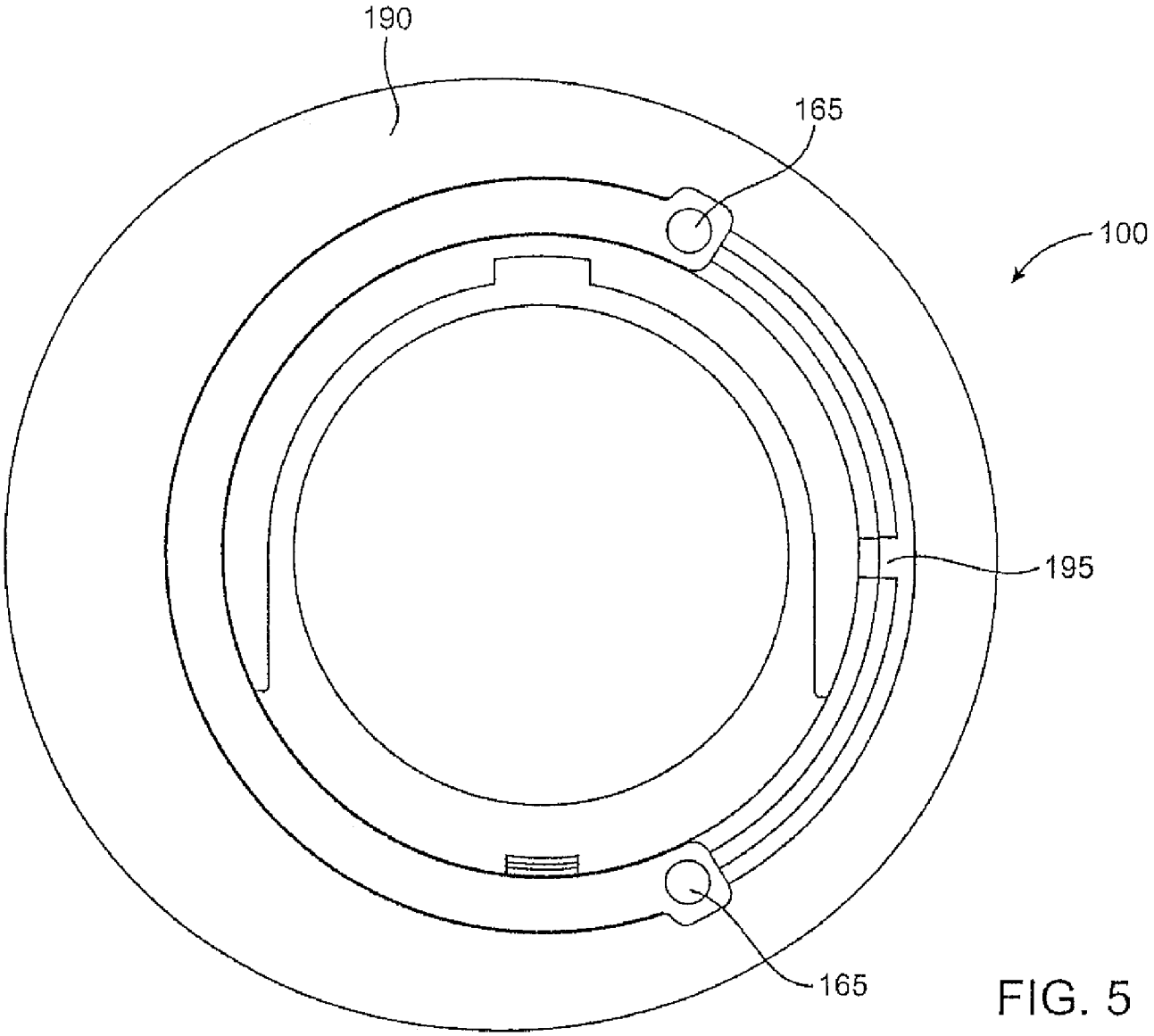
FIG. 5 is a top of the headrest depicted in FIG. 4.
Figure 6:
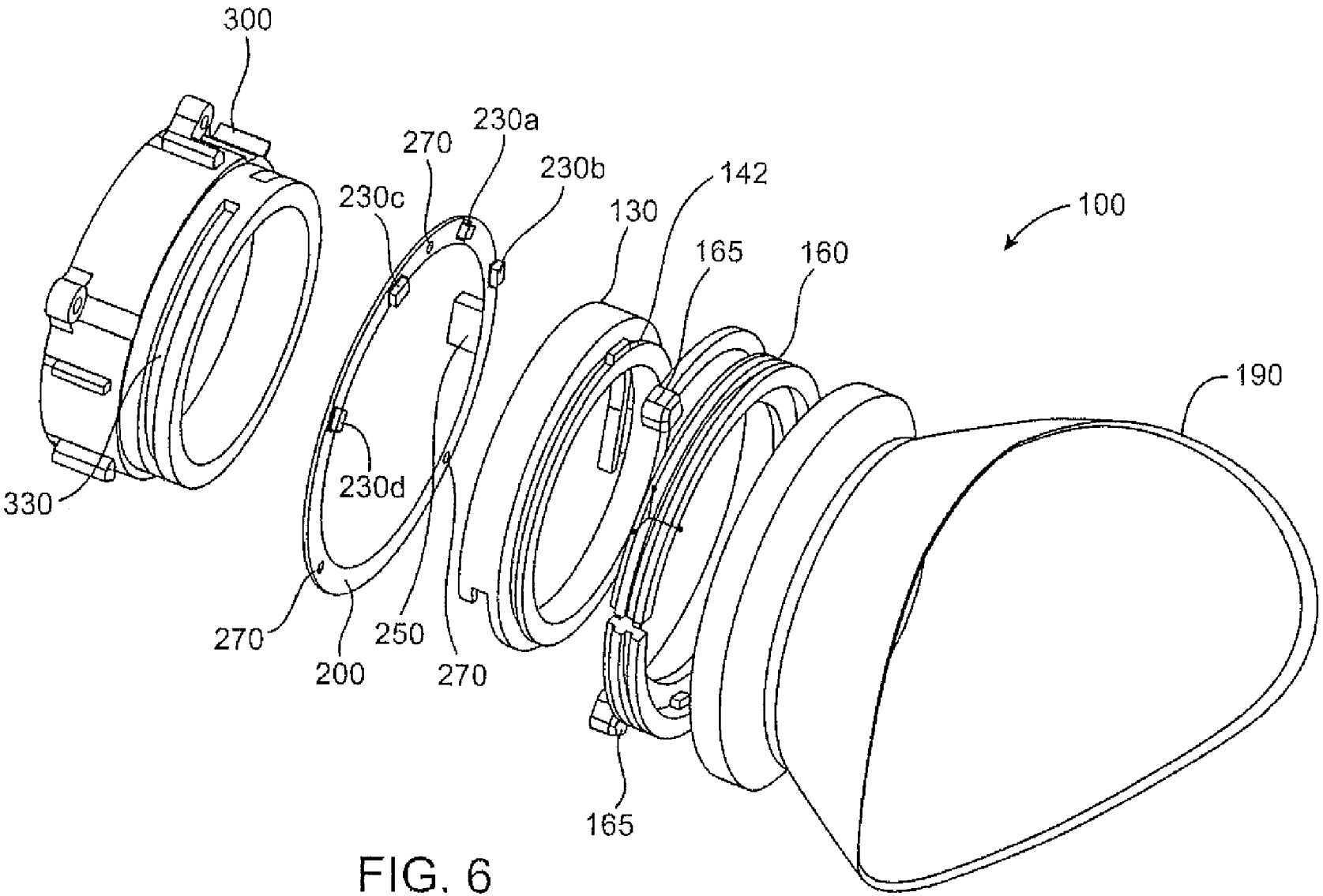
FIG. 6 is an exploded view of a headrest and associated OI according to another embodiment.
Figure 7:
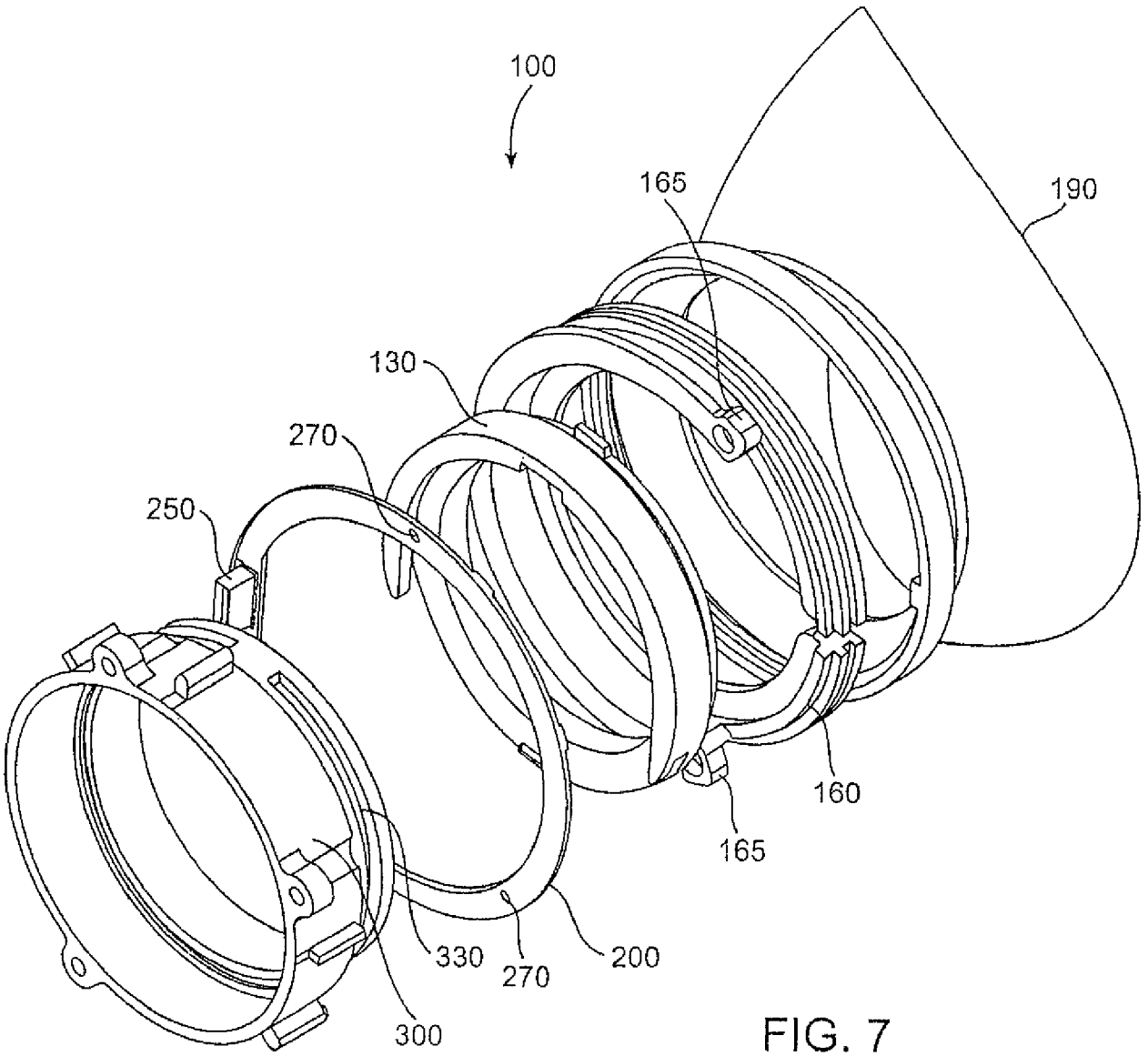
FIG. 7 is an exploded view of the headrest of FIG. 5 taken from another angle.

FIGS. 4 and 5 show another embodiment of a headrest in the form of an eyecup 100. The eyecup 100 includes three main components: 1) an OI connector 130; 2) a rotation ring 160; and 3) a flexible cup 190. The OI connector 130 includes an alignment slot 135, which is designed to line up with an alignment tab in the OI. The connector 130 also includes a mechanical stop 137, which is designed t stop the rotation of the rotation ring 160. The rotation ring 160 is attached to the OI connector 130 by axially mating with the channel 142 (better seen in FIG. 6) formed into the distal end of the OI connector 130. The OI connector 130 also includes a semicircular lip 139 that is designed to mate with a semicircular slot 330 (shown in FIGS. 6 and 7) in the OI.

The rotation ring 160 includes magnet cavities 165 for placement of magnets therein. The eyecup 100 is shown with only two magnet cavities 165, but there can two, three, four, five, six, seven, eight, nine, or more such cavities. The rotation ring 160 also includes an alignment slot 167 for proper alignment with the flexible cup 190. The proximal side of the rotation ring 160 is mated with the channel 142 and can revolve axially around the OI connector 130, restricted in its evolution only by the mechanical stop 137.

The flexible cup 190 includes an alignment lip 195 for aligning the cup 190 with the rotation ring 160. The mating of the alignment lip 195 and the alignment slot 167 fixes the cup 190 to the rotation ring 160 so that the cup 190 cannot revolve axially around the rotation ring 160. Thus, when the rotation ring 160 is manually rotated or revolved, the flexible cup 190 revolves with it. The flexible cup 190 includes an apex 197, which is designed to align with the temporal side of an eye socket.

In the eyecup 100, magnets (not shown) are placed in the magnet cavities 165. When the eyecup 100 is attached to faceplate 300 of an OI, as shown in an exploded view in FIGS. 6 and 7, one of the magnets lines up with one of at least two Hall-effect switches 230 mounted on a circuit board 200, which is integrated with the faceplate 300. The printed circuit board 200 has the Hall-effect switches 230 mounted on it in a predetermined layout. The Hall-effect switches can detect the presence of a magnetic field. The circuit board 200 also includes a Zero Insertion Force (ZIF) connector 250 for a ribbon cable. The ZIF connector 250 is the interface between the circuit board 200 and the microprocessor (not shown) that is in the OI, thus providing a path for the transmission of data from the circuit board 200 to the microprocessor. Alignment holes 270 ensure that the circuit board 200 is properly mounted and aligned with the faceplate 300.

The rotation ring is rotated in one direction in order to use the eyecup 100 on the right eye of a patient, and it is rotated in the opposite direction in order to use the eyecup 100 on the left eye of a patient. Thus, when the eyecup is used on the right eye of a patient, only one of the magnets aligns with the Hall-effect switch at, for example, position 230a, while the other magnet does not align with any Hall-effect switch. When the eyecup is used on the left eye of the patient, again only one of the magnets aligns with another Hall-effect switch at, for example position 230c, while the other magnet does not align with any Hall-effect switch. Thus, the microprocessor is able to process information about the eye on which the OI device is being used based on the Hall-effect switch that is activated. In the above examples, if Hall-effect switch at position 230a is switched, that means the eyecup 100 is aligned to measure the right eye of the patient. Likewise, if the Hall-effect switch at position 230c is switched, that means the eyecup 100 is aligned to measure the left eye of the patient. The OI may need to adjust itself based on which eye is being examined. Thus, armed with information about the eye being examined, the microprocessor can calibrate the OI device for appropriate measurement using calibration software integrated into the microprocessor.

In another embodiment, the invention relates to a system including an OI and one or more detachable headrests. The detachable headrest includes a microprocessor and programming including memory for storing data, such as a unique identifier for identifying the type of headrest. The headrest includes an interface for communicating with the microprocessor of the OI. For example, the OI can include a serial port for connection with the headrest. This enables communication and transfer of data between the OI and the headrest. Upon connection, the OI can receive the headrest's unique identifier and can use that information to determine the type of headrest it is. In addition, the headrest can individually be programmed to contain unique information about the patient including ID, prescription or other patient orders such as frequency of measurement required. This programming can be internal or external to the headrest (e.g., with the headrest attached to the OI or with the headrest interfaced to some other external programming device through an interface (IrDA, serial, USB, etc.)). Information programmed into the memory of the headrest can be passed through the interface to the OI. The interface between the OI and headrest can be an IrDA, serial, USB, optical interface, an RF interface or an extension of photodiodes and detectors (linear array) reading a bar-code, which is integrated into or onto the headrest with a label.

In another embodiment, the headrest can include a magnetic strip that is preprogrammed with certain information, such as the age of the patient or any other identifying indicia of the patient, whether the headrest is being used for critical care or ophthalmology, etc. The OI can include a sensor or reader to read the magnetic strip on the headrest and to receive the information contained in the magnetic strip.

In yet another embodiment, a radio transmission programmer can be integrated into the headrest, and a receiver integrated into the OI.

The OI can include a keypad to enter data or program the OI, such as the pupilometers disclosed in U.S. Pat. Nos. 6,116,736 and 6,260,968, as well as U.S. application Ser. No. 09/711,675, filed Nov. 9, 2000. For example, the patient's identifier can be programmed into the OI, so that the OI rejects any headrest that is programmed with a different identifer. Alternatively, the microprocessor of the OI can be programmed to deactivate the headrest after a set number of uses, or if the patient identifier in the OI does not match the identifier that has been programmed into the headrest. This system reduces the risk of cross-contamination (body fluids, etc.) due to improper use of headrests between patients.

While the invention is susceptible to various modifications and alternative forms, specific examples thereof have been shown by way of example in the drawings and are herein described in detail. It should be understood, however, that the invention is not limited to the particular forms disclosed, but to the contrary, the invention is to cover all modifications, equivalents, and alternatives falling with the spirit and scope of the appended claims.

We claim:

[1. A headrest for use with an ophthalmic instrument, the headrest comprising:

an ophthalmic instrument connector;

a rotation ring connected to the ophthalmic instrument connector, the rotation ring comprising at least one receptacle that receives a detection element, wherein the detection element comprises a radio frequency transmitter; and an eyecup connected to the rotation ring.]

[2. The headrest of claim 1, wherein the ophthalmic instrument connector comprises a proximal end and a distal end, the proximal end comprising a substantially semicircular lip that is configured to mate with a substantially semicircular slot of an ophthalmic instrument.]

[3. The headrest of claim 2, wherein the proximal end of the ophthalmic instrument connector comprises a mechanical stop that stops the rotation of the rotation ring.]

[4. The headrest of claim 1, wherein the rotation ring comprises an alignment slot that mates with an alignment lip on the eyecup.]

[5. The headrest of claim 1, wherein the eyecup comprises a neck portion and a cup portion distal the neck portion, the neck portion comprising a ring that connects to the rotation ring, and the cup portion comprising a flexible cup having an apex that aligns with a temporal side of an eye socket.]

[6. The headrest of claim 1, wherein the eyecup is rotationally locked to the rotation ring and the rotation ring is rotatably coupled to the ophthalmic instrument and can be revolved around the ophthalmic instrument connector such that the eyecup rotates with the rotation ring.]

*7. A headrest for use with a handheld pupilometer, the headrest comprising:*

*a connector with a central aperture and an attachment slot and connection lip formed integrally with the connector, said attachment slot and connection lip configured for connecting the headrest to the handheld pupilometer;*

*one or more arms projecting directly from the connector;*

*one or more face pads at the end of the one or more arms, said one or more face pads formed integrally with said one or more arms respectively; and*

*a detection element, wherein the detection element comprises a radiofrequency element, wherein the radiofrequency element comprises a radiofrequency transmitter capable of communicating with a radiofrequency receiver in the handheld pupilometer.*

* * * * *